United States Patent [19]

Wilson

[11] 3,932,807

[45] Jan. 13, 1976

[54] GAS SENSITIVE DEVICES

[75] Inventor: Ronald Wilson, Calver, England

[73] Assignee: National Research Development Corporation, London, England

[22] Filed: Mar. 29, 1974

[21] Appl. No.: 456,217

[30] Foreign Application Priority Data
Mar. 30, 1973 United Kingdom............... 15576/73

[52] U.S. Cl. ........... 324/71 SN; 340/237 S; 23/254; 73/23
[51] Int. Cl.² .................. G01N 27/00; G08B 21/00; G01N 31/00
[58] Field of Search ............. 324/71 SN; 340/237 S; 23/254; 73/23

[56] References Cited
UNITED STATES PATENTS
3,695,848  10/1972  Taguchi .......................... 324/71 SN
3,699,803  10/1972  Sumi et al. ....................... 324/71 SN Primary Examiner—Alfred E. Smith
Assistant Examiner—Rolf Hille
Attorney, Agent, or Firm—Cushman, Darby and Cushman

[57] ABSTRACT

In a system for detecting a gas or vapour by virtue of its effect on the electrical conductivity of a semiconducting material which is maintained at a suitable operating temperature by an electric resistance heater, the heater has an appreciable temperature coefficient of resistance and is connected in a bridge circuit, the current supplied to the bridge being automatically controlled in response to variations of its out-of-balance voltage so as to maintain constancy of the resistance of the heater and hence of the operating temperature.

3 Claims, 2 Drawing Figures

FIG. I.

GAS SENSITIVE DEVICES

This invention relates to gas detection systems of the kind comprising a gas-sensitive resistor consisting of semiconducting material exposed for contact with an atmosphere under test, an electric resistance heater closely juxtaposed with the gas-sensitive resistor and operable to heat it to temperatures at which the electrical conductivity of the semiconducting material is dependent on the concentration of a particular gaseous substance in an atmosphere to which the material is exposed, and detecting means responsive to changes in the resistance of the gas-sensitive resistor. The detecting means may be arranged to provide a continuously variable measure of the concentration of the relevant substance in an atmosphere under test, or may be arranged to give an alarm or operate a control in response to the occurrence of specific values of this concentration.

In known systems of this kind, it has been usual to employ very simple arrangements for supplying power to the heater from a source of nominally constant voltage. While such arrangements may be satisfactory when using conventional semiconducting materials of low sensitivity (ie exhibiting relatively small changes in conductivity for a given change in concentration of the relevant gaseous substance), they have been found to be inadequate if accurate results are to be obtained when using recently developed semiconducting materials of high sensitivity, for example such as are described in the Specification of copending U.S. patent application Ser. No. 409,453 filed Oct. 25, 1973 now U.S. Pat. No. 3,865,550. This is because in such a case the operation of the detecting means is likely to be materially affected by variations in the temperature of the gas-sensitive resistor, which may arise either from variations in the ambient temperature or changes in the actual voltage of the source from which power is supplied to the heater; the latter possibility is particularly relevant in connection with systems used in portable instruments having a power source constituted by an internal battery.

It is therefore an object of the present invention to provide a gas detection system of the kind specified incorporating an improved arrangement for supplying power to the heater.

According to the invention, in a gas detection system of the kind specified the heater has an appreciable temperature coefficient of resistance and is connected in one arm of a bridge circuit having input terminals via which current is arranged to be supplied to the bridge circuit in operation and output terminals between which a voltage appears when current is supplied to the bridge circuit with the bridge circuit unbalanced, the system including means operative in response to variations in said voltage for automatically controlling the current supplied to the bridge circuit so that in normal operation the resistance of the heater is maintained substantially constant at a value corresponding to a desired operating temperature of the gas-sensitive resistor.

Preferably the detecting means in a system according to the invention includes a further circuit connected between said input terminals and incorporating the gas-sensitive resistor, the further circuit being operative to provide an output voltage dependent on the resistance of the gas-sensitive resistor.

One arrangement in accordance with the invention will now be described by way of example with reference to the accompanying drawings, in which.

Figure 1:
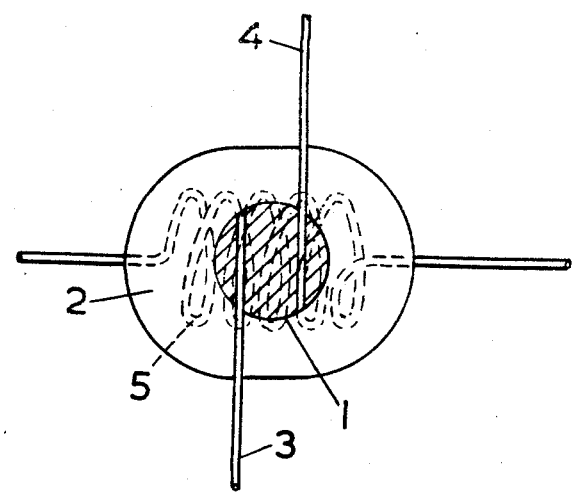
FIG. 1 shows a gas-sensitive device.

The device shown in FIG. 1, which in use is mounted so that it can be exposed to an atmosphere to be tested, incorporates a gas-sensitive resistor 1 in the form of a film of semiconducting material deposited on the surface of a fused glass bead 2 which is of approximately spherical shape of diameter 1 mm, the resistor 1 being provided with leads 3 and 4 constituted by wires partly embedded in the bead 2. The device further incorporates an electric resistance heater 5 for maintaining the resistor 1 at a suitable operating temperature; the heater 5 is constituted by a length of platinum-rhodium wire the central part of which is in the form of a coil embedded in the bead 2, and at normal temperatures has a resistance of about 1.4 ohms. The material of the resistor 1 is chosen so that at the operating temperature its electrical conductivity will be strongly dependent on the concentration in the atmosphere under test of a specific gas or vapour to be detected, the material preferably being an activated metal oxide such as is disclosed in the Specification referred to above. When using such an activated oxide, a suitable operating temperature will normally lie in the range 400°–700°C, the value in a particular case being dependent on the composition of the oxide and the gas or vapour to be detected, and the resistance of the resistor 1 at the operating temperature will typically be of the order of thousands or tens of thousands of ohms. Heating of the device to a temperature in the quoted range requires a voltage in the range 0.9–1.6 volts to be applied across the heater 5, the resultant increase in the resistance of the heater 5 bringing it to a value in the range 2–3 ohms.

Figure 2:
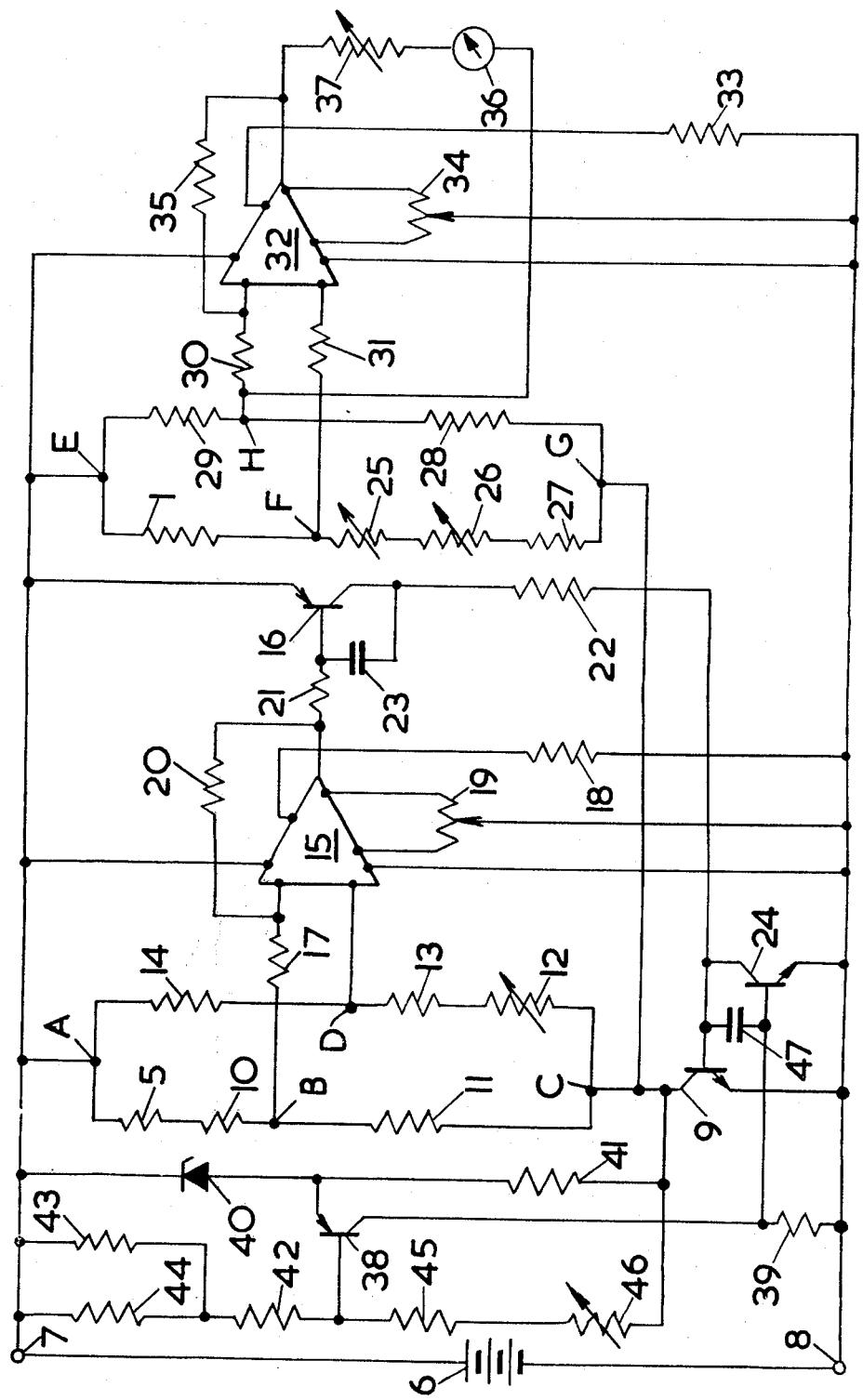
FIG. 2 is a circuit diagram of a gas detection system incorporating a device as shown in FIG. 1 and suitable for embodiment in a portable instrument.

Referring now to FIG. 2, the gas detection system is arranged to be energised by a battery 6 consisting of three nickel-cadmium cells, which in operation is connected between a positive supply terminal 7 and a negative supply terminal 8; the voltage of the battery 6 when fully charged is 4.05 volts, but this drops to a value of 3.35 volts as the battery 6 discharges. The heater 5 of the device shown in FIG. 1 is connected in a bridge circuit ABCD, the terminals A and C of the bridge circuit being respectively connected to the terminal 7 and to the collector of an N-P-N transistor 9 (Motorola type MPS U06) having a power rating of one watt; the emitter of the transistor 9 is connected to the terminal 8, so that in operation there is supplied to the bridge circuit via the terminals A and C a current whose value is dependent on the base current of the transistor 9. The heater 5 is connected in the arm AB of the bridge circuit, a resistor 10 being connected in series with the heater 5 in this arm in cases where the heater voltage necessary to give the required operating temperature is less than 1.4 volts; the resistor 10 is omitted in cases where the required heater voltage is above this value. The remaining arms BC, CD, and DA of the bridge circuit respectively consist of a resistor 11, the series combination of a variable resistor 12 (maximum value 20 ohms) and a fixed resistor 13 (having a value selected in the range 150 to 200 ohms), and a resistor 14 (240 ohms).

The arrangement is suitable for operating the heater 5 at any chosen temperature in the range 400°–700°C; for any desired operating temperature, the values of the resistors 10 (if present), 11 and 13 are chosen, in each case from a small number of standard values, so that when the heater 5 has a resistance corresponding to the desired operating temperature the bridge circuit can be accurately balanced by appropriate adjustment of the resistor 12. It will be appreciated that the required values for the resistors 10 and 11 will always be relatively small, so that most of the current supplied to the bridge circuit will flow through arms AB and BC.

The base current of the transistor 9 is arranged in normal operation to be controlled automatically in response to the voltage appearing between the terminals B and D, by means of a servo loop comprising a differential operational amplifier 15 (Intersil type 8021C) and a P-N-P transistor 16 (Mullard type BCY72). The terminal B is connected via a resistor 17 (100 ohms) to the inverting input terminal of the amplifier 15, while the terminal D is connected directly to the non-inverting input terminal of the amplifier 15. The positive and negative supply terminals of the amplifier 15 are respectively connected to the terminals 7 and 8, the current set terminal of the amplifier 15 is connected to the terminal 8 via a resistor 18 (100 kilohms), the input offset adjustment terminals of the amplifier 15 have connected between them a variable potentiometer 19 (100 kilohms) whose tapping point is connected to the terminal 8, and a feedback resistor 20 (1 Megohm) is connected between the output and inverting input terminals of the amplifier 15. The amplifier 15 will not operate satisfactorily if the voltage between its positive supply and input terminals falls below about 1.4 volts, and it is for this reason that the resistor 10 is included in the bridge circuit when the required heater voltage is less than this amount. The output terminal of the amplifier 15 is connected via a resistor 21 (240 ohms) to the base of the transistor 16, whose emitter is connected to the terminal 7, and the collector of the transistor 16 is connected via a resistor 22 (75 ohms) to the base of the transistor 9; a capacitor 23 (0.1 microfarad) is connected between the base and collector of the transistor 16 to suppress any tendency to oscillation. It will be noted that the system includes an N-P-N transistor 24 having its collector and emitter respectively connected to the base and emitter of the transistor 9; the purpose of the transistor 24 will be explained below, it being sufficient to observe here that in normal operation of the system the transistor 24 is in a virtually cutoff condition so that its presence may be disregarded.

In normal operation, the servo loop functions to control the current supplied to the bridge circuit in such a manner as to maintain the resistance of the heater 5 substantially constant at a value, corresponding to the desired operating temperature, determined by the values of the resistors 10 (if present), 11 and 13 and the setting of the resistor 12. Ideally the arrangement would be such as to maintain the bridge circuit perfectly balanced, but in practice it is preferable, in order to ensure stability, to set the potentiometer 19 which constitutes the input offset control of the amplifier 15 so that the terminal D is held approximately one millivolt positive with respect to the terminal B. The stability of the temperature control system is dependent on the stability of the resistors incorporated in the bridge circuit. Since the resistors 10 (if present) and 11 carry an appreciable current, they are preferably wound from wire having a low temperature coefficient of resistivity and are made physically large enough to ensure that their temperatures in normal operation are not greatly above ambient temperature. The resistors 13 and 14 may suitably be of metal film types, while the resistor 12 may suitably be of the "Cermet" type.

The resistor 1 of the device shown in FIG. 1 is connected in a second bridge circuit EFGH, the terminals E and G of which are respectively connected to the terminals A and C; the arms EF, FG, GH and HE of the second bridge circuit respectively consist of the resistor 1, the series combination of two variable resistors 25 (maximum value 5 kilohms) and 26 (maximum value 1 kilohm) and a fixed resistor 27, a resistor 28 (470 ohms) and a resistor 29 (470 ohms). The bridge circuit EFGH is arranged so that in normal operation it will be balanced if the resistor 1 is exposed to an atmosphere from which the gas or vapour to be detected is absent, this requiring appropriate selection of the value of the resistor 27 in accordance with the composition and desired operating temperature of the resistor 1, and appropriate adjustment of the coarse and fine balance controls constituted respectively by the resistors 25 and 26. The terminals H and F are respectively connected via resistors 30 (10 kilohms) and 31 (1 kilohm) to the inverting and non-inverting input terminals of a second differential operational amplifier 32 (Intersil type 8021C). The positive and negative supply terminals of the amplifier 32 are respectively connected to the terminals 7 and 8, the current set terminal of the amplifier 32 is connected to the terminal 8 via a resistor 33 (100 kilohms), the input offset adjustment terminals of the amplifier 32 have connected between them a variable potentiometer 34 (100 kilohms) whose tapping point is connected to the terminal 8, and a feedback resistor 35 (10 kilohms) is connected between the output and inverting input terminals of the amplifier 32. A current meter 36 and variable resistor 37 (maximum value 10 kilohms) are connected in series between the output terminal of the amplifier 32 and the terminal H, the potentiometer 34 being adjusted so that the current flowing through the meter 36 will be zero when the bridge circuit EFGH is balanced. When the resistor 1 is exposed to an atmosphere in which the gas or vapour to be detected is present, the resultant change in its resistance will cause an out-of-balance voltage to appear between the terminals F and H, thereby causing to flow through the meter 36 a current whose magnitude will depend on the concentration of the relevant gas or vapour; the calibration of the reading of the meter 36 in terms of this concentration may be set by adjustment of the resistor 37.

The arrangement described above has the advantage of providing a much more stable voltage supply for the bridge circuit EFGH than would be the case if this circuit were energised directly from the battery 6, since the operation of the servo loop is such that the voltage appearing between the terminals A and C is substantially independent of the voltage of the battery 6. Thus, while avoiding the complexity of providing a separate voltage stabiliser the arrangement ensures that the reading of the meter 36 for a given concentration of the gas or vapour to be detected will not be significantly affected by changes in the voltage of the battery 6. The operation of the servo loop will of course cause some variation in the voltage appearing between the terminals A and C as the ambient temperature varies, but the range of variation of the voltage from this cause is sufficiently small for the resultant effect on the reading of the meter 36 to be tolerable in practice.

The description so far has dealt only with the normal operating condition of the system, in which the gas-sensitive device is maintained at an elevated temperature; it remains to consider what happens when the system is switched on with the gas-sensitive device initially at ambient temperature. Rapid heating up of the device to its normal operating temperature can cause a temporary change in the resistance characteristics of the resistor 1, requiring the allowance of an appreciable recovery time (possibly up to 15 minutes) before the instrument will give correct readings. The length of this recovery time can be reduced by restricting the rate of heating, and in the present case this is achieved by providing a system which is operative to limit the current supplied to the bridge circuit ABCD so that the voltage appearing between the terminals A and C when the heater 5 is below the desired operating temperature will only slightly exceed the voltage appearing between the terminals A and C when the heater 5 is at the desired operating temperature; in the absence of such a system, the relatively large out-of-balance voltage initially appearing between the terminals B and D when the system is switched on would cause the transistor 9 to be driven into a saturated condition so that the voltage appearing between the terminals A and C would be nearly equal to the voltage of the battery 6.

The limiting system includes the transistor 24 (Mullard type BC109) and a P-N-P transistor 38 (Mullard type BCY71) whose collector is connected to the base of the transistor 24 and via a resistor 39 (ten kilohms) to the terminal 8. The emitter and base of the transistor 38 are respectively connected to points on two potential dividers connected between the terminals A and C, the arrangement being such that the transistor 38, and hence also the transistor 24, will conduct if the voltage appearing between these terminals exceeds by about 0.1 volt the value which it has when the heater 5 is at the desired operating temperature. Thus the emitter of the transistor 38 is connected to the terminal A via a reference diode 40 (Mullard type BZY88-ClV3), and is connected to the terminal C via a resistor 41 (330 ohms); the base of the transistor 38 is connected to the terminal A via a resistor 42 (12 kilohms) in series with the parallel combination of a thermistor 43 (Standard Telephones and Cables Type G14) and a resistor 44 (39 kilohms), and is connected to the terminal C via a fixed resistor 45 (5.6 kilohms) in series with a variable resistor 46 (maximum value 5 kilohms) whose setting determines the precise point at which the transistor 38 will conduct. The limiting system operates so that any tendency for the voltage appearing between the terminals A and C to exceed the value at which the transistor 38 conducts results in a reduction in the drive to the transistor 9 brought about by a low-impedance shunt constituted by the transistor 24, thereby appropriately limiting the current supplied to the bridge circuit ABCD. A capacitor 47 (0.1 microfarad) is connected between the collector and base of the transistor 24 to suppress any tendency to oscillation.

As noted above, the voltage appearing between the terminals A and C in the normal operating condition will vary with the ambient temperature, and it is therefore necessary for the limiting system to have an approximately matching temperature coefficient so that as the ambient temperature varies the differential between that voltage and the voltage at which the limiting action occurs will be maintained approximately constant. This is achieved in the circuit described by virtue of an appropriate balance between the characteristics of the diode 40 and the impedance network constituted by the thermistor 43 and resistors 42 and 44.

I claim:
1. A gas detection system comprising:
   a gas-sensitive resistor consisting of semiconducting material exposed for contact with an atmosphere under test;
   a bridge circuit in one arm of which is connected an electric resistance heater having an appreciable temperature coefficient of resistance, said heater being closely juxtaposed with the gas-sensitive resistor and being operable to heat the gas-sensitive resistor to temperatures at which the electrical conductivity of the semiconducting material is dependent on the concentration of a particular gaseous substance in an atmosphere to which said material is exposed;
   means for enabling current to be supplied to said bridge circuit via a pair of input terminals of the bridge circuit, said bridge circuit having a pair of output terminals between which a voltage appears when current is supplied to the bridge circuit via said input terminals with the bridge circuit unbalanced;
   means operative in response to variations in said voltage for automatically controlling the current supplied to said bridge circuit via said input terminals so that in normal operation the resistance of said heater is maintained substantially constant at a value corresponding to a desired operating temperature of said gas-sensitive resistor; and
   detecting means responsive to changes in the resistance of said gas-sensitive resistor.

2. A gas detection system according to claim 1, in which said detecting means includes a further circuit connected between said input terminals and incorporating said gas-sensitive resistor, said further circuit being operative to provide an output voltage dependent on the resistance of said gas-sensitive resistor.

3. A gas detection system according to claim 1, further including means, operative in a starting condition of the system in which said heater is being heated up to its normal operating temperature, for automatically limiting the current supplied to said bridge circuit via said input terminals so that the voltage which appears between said input terminals in said starting condition is only slightly greater than the voltage which appears between said input terminals in the normal operating condition of the system.

* * * * *